/

US 6,881,698 B2

(12) United States Patent
Bonnet et al.

(10) Patent No.: US 6,881,698 B2
(45) Date of Patent: Apr. 19, 2005

(54) ION LIQUIDS DERIVED FROM LEWIS ACID BASED ON TITANIUM, NIOBIUM, TANTALUM, TIN OR ANTIMONY, AND USES THEREOF

(75) Inventors: Phillippe Bonnet, Lyons (FR); Eric Lacroix, Amberieux d'Azergues (FR); Jean-Pierre Schirmann, Paris (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/258,481

(22) PCT Filed: Apr. 24, 2001

(86) PCT No.: PCT/FR01/01245

§ 371 (c)(1),
(2), (4) Date: May 13, 2003

(87) PCT Pub. No.: WO01/81353

PCT Pub. Date: Nov. 1, 2001

(65) Prior Publication Data

US 2004/0033892 A1 Feb. 19, 2004

(30) Foreign Application Priority Data

Apr. 26, 2000 (FR) .......................................... 00 05275

(51) Int. Cl.[7] ................................................ B01J 31/00
(52) U.S. Cl. ...................... 502/162; 502/164; 502/167; 502/168; 502/169; 570/166; 570/167; 570/168; 570/169
(58) Field of Search ................................ 502/162, 164, 502/167, 168, 169; 570/166, 167, 168, 169

(56) References Cited

U.S. PATENT DOCUMENTS 5,093,296 A * 3/1992 Frame et al. ............... 502/155
5,180,484 A * 1/1993 Frame et al. ............... 208/184
5,994,602 A   11/1999 Abdul-Sada et al.
6,365,301 B1   4/2002 Michot et al. .............. 429/307

FOREIGN PATENT DOCUMENTS

| FR | 2 611 700 | 9/1988 |
|----|-----------|--------|
| FR | 2 626 572 | 8/1989 |
| WO | WO 95/21806 | 8/1995 |
| WO | WO 96/18459 | 6/1996 |
| WO | WO 99/40025 | 8/1999 |
| WO | WO 00/20115 | 4/2000 |
| WO | WO 00/56700 | 9/2000 |

OTHER PUBLICATIONS

J. Robinson and R.A. Osteryoung, "An Electrochemical and Spectroscopic Study of Some Aromatic Hydrocarbons in the Room Temperature Molten Salt System Aluminum Chloride–n–Butylpyridinium Chloride", Journal of the American Chemical Society, vol. 101:2, pp. 323–327, dated Jan. 17, 1979.

John S. Wilkes, et al., "Dialkylimidazolium Chloroaluminate Melts: A New Class of Room–Temperature Ionic Liquids for Electrochemistry, Spectroscopy, and Synthesis", Inorg. Chem. vol. 21, No. 3, pp. 1263–1264, dated 1982.

* cited by examiner

Primary Examiner—Mark L. Bell
Assistant Examiner—J. Pasterczyk
(74) Attorney, Agent, or Firm—Smith, Gambrell & Russell, LLP

(57) ABSTRACT

The ionic liquids according to the invention result from the reaction of a halogenated or oxyhalogenated Lewis acid based on titanium, niobium, tantalum, tin or antimony with an organic salt of formula $X^+A^-$ in which $A^-$ is a halide anion and $X^+$ a quaternary ammonium, quaternary phosphonium or ternary sulphonium cation. These liquids can be used in particular in the liquid-phase fluorination using HF of saturated or unsaturated compounds having C—Cl groups.

26 Claims, No Drawings

ION LIQUIDS DERIVED FROM LEWIS ACID BASED ON TITANIUM, NIOBIUM, TANTALUM, TIN OR ANTIMONY, AND USES THEREOF

FIELD OF THE INVENTION

The present invention relates to ionic liquids and has more particularly as subject-matter ionic liquids based on titanium, niobium, tantalum, tin or antimony.

BACKGROUND OF THE INVENTION

The ionic liquids as considered in the present patent application are nonaqueous salts with an ionic nature which are liquid at moderate temperatures and which result from the reaction between an organic salt and an inorganic compound, A certain number of ionic liquids are already known. Thus, in J. Am. Chem. Soc. 101, 2, 323–327 (1979), Osteryoung et al. have demonstrated that the mixture of butylpyridinium chloride (A) and of aluminium chloride $AlCl_3$ (B) is liquid at 40° C. over a wide range of compositions (A/B molar ratio ranging from 1/0.75 to 1/2). In Inorg. Chem. 21, 1263–1264, Wilkes et al. have shown that the compounds resulting from the reaction between $AlCl_3$ and a dialkylimidazolium chloride, such as 1-butyl-3-methylimidazolium chloride, are liquid at room temperature, also for the same range of compositions described above. In this example of an ionic liquid, the dialkylimidazolium constitutes the cation and $AlCl_4$ the anion. Other anions, such as nitrate, acetate or tetrafluoroborate anions, can be used (see the publication WO 9618459).

Due to their wide electrochemical window, ionic liquids can be used as battery electrolytes. They are also particularly useful in catalysis, as they are excellent solvents for organometallic compounds. Thus, for example, Patent Applications FR 2,626,572 and WO 9521806 disclose the use of the abovementioned compounds based on chloroaluminate in the alkylation, in two-phase catalysis, of aromatic or isoparaffin compounds.

DETAILED DESCRIPTION OF THE INVENTION

A subject-matter of the invention is now ionic liquids derived from Lewis acids based on titanium, niobium, tantalum, tin or antimony. These ionic liquids find applications in catalysis and can also have properties of solvating organometallic compounds capable of being used in two-phase catalysis.

The ionic liquids according to the invention, which are aprotic nonaqueous ionic compounds which are liquid over a range of moderate temperatures (preferably below 120° C.) at atmospheric pressure, are obtained by reaction of a halogenated or oxyhalogenated Lewis acid based on titanium, niobium, tantalum, tin or antimony with a salt of general formula $X^+A^-$ in which $A^-$ denotes a halide (bromide, iodide and, preferably, chloride or fluoride) or hexafluoroantimonate ($SbF_6^-$) anion and X' a quaternary ammonium, quaternary phosphonium or ternary sulphonium cation.

The halogenated Lewis acid based on titanium, niobium, tantalum, tin or antimony can be a chlorinated, brominated, fluorinated or mixed derivative, for example a chlorofluorinated acid. Mention may more particularly be made of the chlorides, fluorides or chlorofluorides with the following formulae:

$TiCl_xF_y$ with $x+y=4$ and $0 \leq x \leq 4$ $TaCl_xF_y$ with $x+y=5$ and $0 \leq x \leq 4$ $NbCl_xF_y$ with $x+y=5$ and $0 \leq x \leq 5$ $SnCl_xF_y$ with $x+y=4$ and $1 \leq x \leq 4$ $SbCl_xF_y$ with $x+y=5$ and $0 \leq x \leq 5$ Mention may be made, as examples of such compounds, of the following compounds: $TiCl_4$, $TiF_4$, $TaCl_5$, $TaF_5$, $NbCl_5$, $NbF_5$, $SnCl_4$, $SnF_4$, $SbCl_5$, $SbCl_4F$, $SbCl_3F_2$, $SbCl_2F_3$, $SbClF_4$, $SbF_5$ and their mixtures. Use is preferably made of the following compounds: $TiCl_4$, $SnCl_4$, $TaCl_5 + TaF_5$, $NbCl_5 + NbF_5$, $SbCl_5$, $SbFCl_4$, $SbF_2Cl_3$, $SbF_3Cl_2$, $SbF_4Cl$, $SbF_5$ and $SbCl_5 + SbF_5$. Preference is more particularly given to antimony-comprising compounds.

Mention may be made, as examples of oxyhalogenated Lewis acids which can be used according to the invention, of $TiOCl_2$, $TiOF_2$, $SnOCl_2$, $SnOF_2$ and $SbOCl_xF_y$ (x+y=3).

In the salt $X^+A^-$, the cation $X^+$ can correspond to one of the following general formulae:

$R^1R^2R^3R^4N^+$ $R^1R^2R^3R^4P^+$ $R^1R^2R^3S^+$ in which the symbols $R^1$ to $R^4$, which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, it being possible for one or more of these groups also to comprise one or more heteroatoms, such as N, P, S or O.

The ammonium, phosphonium or sulphonium cation $X^+$ can also form part of a saturated or unsaturated or aromatic heterocycle having from 1 to 3 nitrogen, phosphorous or sulphur atoms and can correspond to one or other of the following general formulae:

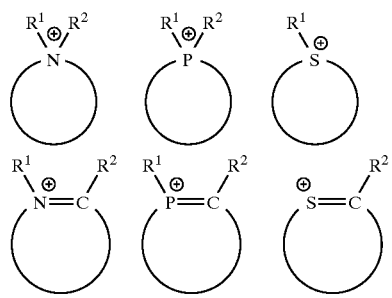

in which $R^1$ and $R^2$ are as defined above.

It would not be departing from the scope of the present invention to use a salt comprising 2 or 3 ammonium, phosphonium or sulphonium sites in their formula.

Mention may be made, as examples of salts $X^+A^-$, of tetraalkylammonium chlorides and fluorides, tetraalkylphosphonium chlorides and fluorides and trialkylsulphonium chlorides and fluorides, and alkylpyridinium chlorides and fluorides, dialkylimidazolium chlorides, fluorides and bromides and trialkylimidazolium chlorides and fluorides. Trimethylsulphonium chloride or fluoride, N-ethyl-pyridinium chloride or fluoride, N-butylpyridinium chloride or fluoride, 1-ethyl-3-methylimidazolium chloride or fluoride and 1-butyl-3-methylimidazolium chloride or fluoride are more particularly valued.

The ionic liquids according to the invention can be prepared in a way known per se by appropriately mixing the halogenated or oxyhalogenated Lewis acid and the organic salt $X^+A^-$ in a molar ratio which can range from 0.5/1 to 3.5/1, preferably from 1/1 to 2.5/1 and more preferably [lacuna] 1/1 to 2/1. A molar ratio rigorously greater than 1/1 is particularly recommended if it is desired to obtain an acidic ionic liquid.

The mixture can be prepared in a reactor of autoclave type, optionally cooled in order to limit the exothermicity of the reaction. It is also possible to control this exothermicity by gradually adding one of the reactants to the other.

When the Lewis acid/organic salt molar ratio is greater than 1/1, it can prove to be useful to heat the reaction medium until the solid has completely dissolved.

As the reactants and the ionic liquid obtained are generally hygroscopic, it is recommended to carry out the synthesis with air and water excluded while using, to this end, the means known to a person skilled in the art.

The ionic liquids according to the invention can be used in all the applications known for compounds of this type. When the Lewis acid/organic salt molar ratio is less than or equal to 1/1, these liquids can be used for their solvating properties (organic synthesis, solvents for organometallic complexes).

When the Lewis acid/organic salt molar ratio is rigorously greater than 1/1, the ionic liquids according to the invention have acidic properties which are advantageous in any catalysis requiring the use of an acid catalyst, for example Friedel-Crafts catalysis and fluorination catalysis.

The ionic liquids according to the invention find a particularly advantageous use in the liquid-phase fluorination by HF of saturated or unsaturated compounds exhibiting C—Cl bonds, such as, for example, $CHCl=CH_2$, $CCl_2=CCl_2$, $CH_2=CCl_2$, $CClH=CCl_2$, $CH_2Cl_2$, $CH_2ClF$, $CCl_3-CH_3$, $CCl_2H-CCl_2H$, $CCl_3-CH_2Cl$, $CCl_3-CHCl_2$, $CF_3-CH_2Cl$, $CCl_3-CH_2-CHCl_2$, $CF_3-CH=CHCl$ or $CCl_3-CH_2-CCl_2-CH_3$.

A liquid-phase fluorination process using an ionic liquid according to the invention as catalyst can be carried out batchwise. The equipment used is then an autoclave, into which the reactants and the catalyst are introduced before the beginning of the reaction, the pressure in the autoclave varying with the progress of the reaction. The molar amount of HF to the molar amount of starting material is between 2 and 50 and preferably between 10 and 30. The duration of the reaction required, which depends on the amount of the reactants involved at the start and on the various operating parameters, can be easily known experimentally.

The fluorination can also be carried out according to a semi-continuous form in equipment composed of an autoclave, surmounted by a simple condenser or by a return column with a reflux condenser, and of a pressure-regulating valve, the pressure being chosen so as to keep the reaction medium in the liquid state. As above, the reactants and the catalyst are introduced beforehand into the reactor but the reaction products with low boiling points (fluorinated products) and the hydrogen chloride (HCl) co-product are continuously extracted during the reaction while the compounds with higher boiling points, such as the starting materials, the intermediate products and the HF, largely flow back in liquid form into the reaction medium by virtue of the condenser (or return column) placed above the reactor.

In accordance with a third embodiment, the fluorination can be carried out continuously in the same equipment as semi-continuously but at least one of the reactants (HF or the starting material) is introduced continuously. In the context of an industrial process, it is preferable to feed the two reactants conjointly. The reaction products are extracted continuously during the reaction, the unconverted reactants flowing back into the reactor. The molar amount of fed HF to the molar amount of fed starting material is at least equal to 2.

The amount of catalyst depends on the operating conditions and on the reaction medium (in the case of a continuous process) but also on the intrinsic activity of the catalyst. This amount is between 0.5 and 90% (molar) of the reaction medium.

When the catalyst used is based on antimony, it may sometimes be advantageous to introduce chlorine in order to keep the antimony in the 5 oxidation state.

The temperature at which the fluorination reaction is carried out (under batchwise and continuous conditions) is generally between 30 and 180° C., preferably between 80 and 130° C.

The pressure at which the reaction is carried out in the semi-continuous or continuous forms is chosen so as to keep the reaction medium in the liquid phase. It is generally between 5 and 50 bar and preferably between 10 and 40 bar; under continuous conditions, if HF constitutes the reaction medium, the operating pressure chosen is generally the saturated vapour pressure of HF at the desired reaction temperature. The temperature of the condenser is determined upon according to the amount and the nature of the products capable of being discharged during the reaction. It is generally between −50 and 150° C. and preferably between 0 and 100° C.

The material of the fluorination reactor must make it possible to operate under the pressure and temperature conditions defined above. It must also withstand the corrosion generated by the hydrogen fluoride. Thus, stainless steel or alloys of Monel, Inconel or Hastelloy type are particularly indicated.

EXAMPLES

The following examples illustrate the invention without limiting it.

Example 1

7.3 g of 1-ethyl-3-methylimidazolium chloride (emim-Cl) were introduced into a Schlenk tube while flushing with argon and then the tube was immersed in ice. Antimony chlorofluoride $SbF_3Cl_2$ was then gradually introduced with stirring. The reaction is exothermic but the ice made it possible to keep the temperature of the tube at approximately 10° C. After having introduced 12.6 g of $SbF_3Cl_2$, corresponding to an $SbF_3Cl_2$/emim-Cl molar ratio of 1/1, the Schlenk tube was heated to approximately 40° C. in order to completely liquefy the ionic liquid formed. Addition of $SbF_3Cl_2$ was then continued at room temperature until the total mass introduced was 25.3 g, corresponding to an $SbF_3Cl_2$/emim-Cl molar ratio of 2/1.

After stirring for 18 hours at room temperature, 32.6 g of an ionic liquid were obtained. This compound was analysed by infrared and raman spectroscopy and exhibits the following main characteristics:

IR
  band at 1600 cm$^{-1}$ (attributable to the C=N bond)
  band between 550 and 600 cm$^{-1}$
Raman
  band at 370 cm$^{-1}$
  band at 174 cm$^{-1}$

Example 2

Example 1 was repeated but replacing, first, antimony chlorofluoride with 31.7 g of an equimolar mixture of tantalum pentafluoride and tantalum pentafluoride and, secondly, emim-Cl with 8.7 g of 1-butyl-3-methylimidazolium chloride (bmim-Cl).

Examples 3 to 14

Other examples of ionic liquids according to the invention obtained in the same way as in Examples 1 and 2 are summarized in the following table. When a liquid is not rapidly obtained, the mixture of Lewis acid and of emim-Cl is heated at 120° C. for 12 hours by immersing the Schlenk tube in an oil bath at 120° C. All the products obtained are liquid below 120° C.

| Example | Lewis acid | Lewis acid/emim-Cl molar ratio | Characteristic (% by mass of metal analyzed) |
|---|---|---|---|
| 3 | $TiCl_4$ | 1/1 | 14 |
| 4 | $TiCl_4$ | 2/1 | 18 |
| 5 | $SnCl_4$ | 1/1 | 29 |
| 6 | $SbF_4Cl$ | 1/1 | 31 |
| 7 | $SbF_4Cl$ | 2/1 | 39 |
| 8 | $NbCl_5$ | 1/1 | 22 |
| 9 | $NbF_5$ | 1/1 | 29 |
| 10 | $NbCl_5 + NbF_5$* | 2/1 | 31 |
| 11 | $SbF_5$ | 1/1 | 33 |
| 12 | $SbF_5$ | 2/1 | 43 |
| 13 | $SbCl_5$ | 1/1 | 27 |
| 14 | $SbCl_5$ | 2/1 | 33 |

*Equimolar mixture of $NbCl_5$ and $NbF_5$

Examples 15 to 24

Other examples of ionic liquids according to the invention obtained in the same way as in examples 1 and 2, but using 1-butyl-3-methylimidazolium chloride (bmim-Cl) as quaternary ammonium salt, are summarized in the following table. When a liquid is not rapidly obtained, the mixture of Lewis acid and of bmim-Cl is heated at 120° C. for 12 hours by immersing the Schlenk tube in an oil bath at 120° C. The products obtained are all liquid below 120° C.

| Example | Lewis acid | Lewis acid/bmim-Cl molar ratio | Characteristic (% by mass of metal analyzed) |
|---|---|---|---|
| 15 | $TiCl_4$ | 1/1 | 13 |
| 16 | $TiCl_4$ | 2/1 | 17 |
| 17 | $TiF_4$ | 1/1 | 16 |
| 18 | $SnCl_4$ | 1/1 | 27 |
| 19 | $NbCl_5$ | 1/1 | 21 |
| 20 | $TaCl_5$ | 1/1 | 34 |
| 21 | $SbCl_5$ | 1/1 | 26 |
| 22 | $SbCl_5$ | 2/1 | 31 |
| 23 | $SbF_5$ | 1/1 | 31 |
| 24 | $SbF_5$ | 2/1 | 40 |

Example 25

12.9 g of sodium hexafluoroantimonate were added to a Schlenk tube comprising 7.3 g of emim-Cl held inn suspension in 30 ml of acetone with vigorous stirring. A milky precipitate was immediately formed and, after stirring for 18 hours, was filtered through Celite®. After having evaporated the acetone under vacuum, a translucent liquid was obtained and the Schlenk tube was immersed in ice in order to cool it, 10.8 g of antimony pentafluoride were added and then the mixture was allowed to return to ambient temperature.

Example 26

30.6 g of the ionic liquid of example 7, 21.5 g of methylene chloride (F30) and 20.8 g of HF were successively charged to a 0.150 liter autoclave made of 316L stainless steel. The autoclave was then immersed in an oil bath at 130° C., the temperature of the condenser being kept at 15–20° C. and the regulating pressure being set at 10 bar absolute. At this pressure, the temperature of the reaction medium was approximately 100° C.

During the reaction, the volatile reaction products were discharged continuously and passed into a water bubbler and then into a dryer before being collected in a stainless steel trap cooled with liquid nitrogen. After reacting for 290 minutes, the autoclave was cooled with circulating water. After returning to room temperature, the autoclave was degassed and the reaction products were washed, dried and trapped as above.

Analysis of the gas phase and of the liquid phase from the various traps showed that 84% of the starting F30 was converted, 69% of which into difluoromethane and 31% of which into chlorofluoromethane (mol %).

Example 27

740 g of trichloroethylene and 102 g of the ionic liquid of example 12 were successively charged to a 1 liter autoclave made of 316L stainless steel equipped with a magnetic stirrer, surmounted by a simple condenser and controlled by a pressure-regulating valve placed at the top of the condenser and via which the reaction products are discharged. The jacket of the autoclave was supplied via an oil bath in order to obtain a temperature of 125° C. in the autoclave and the temperature of the condenser was maintained at 55° C. by supplying water. When the desired temperature was reached, 42 g/h of trichloroethylene, 27 g/h of HF ad 3 g/h of chlorine were continuously supplied. During this test, the opening of the pressure-regulating valve, representative of the gas flow rate at the outlet of the reactor, was continuously monitored.

After a stabilization period of 14 hours, corresponding to an equilibrium composition of the reaction medium in the autoclave being obtained, the opening of the regulating valve became stable. The composition of the gases at the reactor outlet then settled down at 95% F133a ($Cf_3$—$CH_2Cl$) and 5% F132b ($CF_2Cl$—$CH_2Cl$).

After 25 hours of stable operation, the $Cl_2$ supply was cut off. The values of the opening of the valve from the point at which the $Cl_2$ supply was cut off are shown in the following table. It is clearly apparent that, after 20 hours, the opening of the regulating valve has not varied, which corresponds to completely stable operation.

Comparative Example 28

The preceding example was repeated while charging 749 g of trichloroethylene and 53.2 g of $SbCl_5$ in place of the ionic liquid used previously. After obtaining stable operation, the temperature in the autoclave settled down at 125° C.

After 25 hours of stable operation, the chlorine supply was cut off. The opening values of the pressure-regulating valve from the point at which the Cl₂ supply was cut off are shown in the following table. It is seen that, after approximately 4 hours of reaction, the valve closed, which corresponds to a shut down of the reaction.

| Time (hours) | Opening values in % of the pressure-regulating valve after the Cl₂ supply has been cut off | |
|---|---|---|
| | Example 27 | Comparative Example 28 |
| 1 | 10 | 13 |
| 2 | 11 | 13 |
| 3 | 10 | 11 |
| 4 | 10 | 3 |
| 5 | 10 | 0 |
| 7 | 10 | 0 |
| 10 | 12 | 0 |
| 15 | 12 | 0 |
| 20 | 10 | 0 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. Ionic liquid comprising a reaction product of a halogenated or oxygen-containing halogenated Lewis acid containing titanium, niobium, tantalum, tin or antimony with an organic salt of formula $X^+A^-$ in which $A^-$ is a halide anion and $X^+$ a quaternary ammonium, quaternary phosphonium or ternary sulphonium cation.

2. Ionic liquid according to claim 1, wherein the Lewis acid/organic salt molar ratio is between 0.5/1 and 3.5/1.

3. Ionic liquid according to claim 1, wherein the Lewis acid is a titanium, niobium, tantalum, tin or antimony chloride, fluoride or chlorofluoride.

4. Ionic liquid according to claim 1, wherein the cation $X^+$ is an alkylpyridinium, dialkylimidazolium or trialkylimidazolium cation.

5. Ionic liquid according to claim 1, wherein the organic salt $X^+A^-$ is a chloride or a fluoride, the cation $X^+$ corresponding to one of the following formulae:

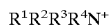

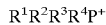

in which the symbols $R^1$ to $R^4$, which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, optionally at least one of these groups comprising at least one heteroatoms.

6. Ionic liquid according to claim 1, wherein the organic salt $X^+A^-$ is a chloride or a fluoride, the cation $X^+$ forming part of a saturated or unsaturated or aromatic heterocycle having from 1 to 3 nitrogen, phosphorus or sulphur atoms and corresponding to at least one of the following formulae:

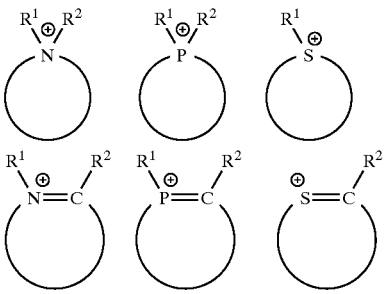

in which $R^1$ and $R^2$, which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, optionally at least one of these groups comprising at least one heteroatom.

7. Ionic liquid according to claim 5, wherein the cation X+ is a tetraalkylammonium, tetraalkylphosphonium, or trialkylsulphonium cation.

8. Process for the liquid-phase fluorination of a saturated or unsaturated compound having C—Cl groups, comprising reacting HF and said saturated or unsaturated compound in the presence of an ionic liquid according to claim 1.

9. Ionic liquid according to claim 2, wherein the Lewis acid is a titanium, niobium, tantalum, tin or antimony chloride, fluoride or chlorofluoride.

10. Ionic liquid according to claim 2, wherein the organic salt $X^+A^-$ is a chloride or a fluoride, the cation $X^+$ forming part of a saturated or unsaturated or aromatic heterocycle having from 1 to 3 nitrogen, phosphorus or sulphur atoms and corresponding to at least one of the following formulae:

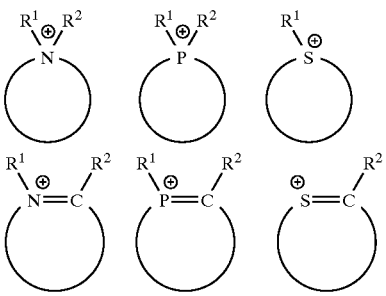

in which $R^1$ and $R^2$, which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, optionally at least one of these groups comprising at least one heteroatom.

11. Ionic liquid according to claim 3, wherein the organic salt $X^+A^-$ is a chloride or a fluoride, the cation $X^+$ forming part of a saturated or unsaturated or aromatic heterocycle having from 1 to 3 nitrogen, phosphorus or sulphur atoms and corresponding to at least one of the following formulae:

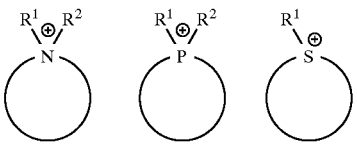

-continued

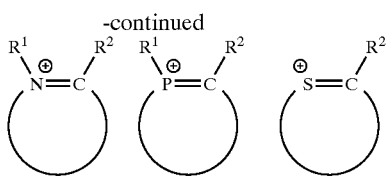

in which R¹ and R², which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, optionally at least one of these groups comprising at least one heteroatom.

12. Ionic liquid according to claim 1, wherein the organic salt $X^+A^-$ is a chloride or a fluoride, the cation $X^+$ forming part of a saturated or unsaturated or aromatic heterocycle having from 1 to 3 nitrogen, phosphorus or sulphur atoms and corresponding to at least one of the following formulae:

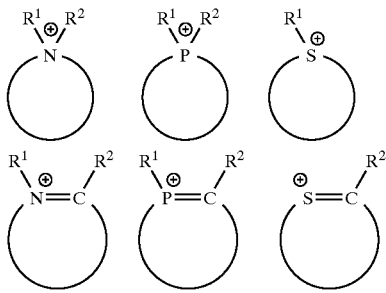

in which R¹ and R², which are identical or different, each denote a saturated or unsaturated, cyclic or noncyclic or aromatic, hydrocarbyl, chlorohydrocarbyl, fluorohydrocarbyl, chlorofluorohydrocarbyl or fluorocarbyl group having from 1 to 10 carbon atoms, optionally at least one of these groups comprising at least one heteroatom.

13. Ionic liquid according to claim 1, wherein the cation X+ is a tetraalkylammonium, tetraalkylphosphonium, or trialkylsulphonium cation.

14. Process for the liquid-phase fluorination of a saturated or unsaturated compound having C—Cl groups, comprising reacting HF and said saturated or unsaturated compound in the presence of an ionic liquid according to claim 2.

15. Process for the liquid-phase fluorination of a saturated or unsaturated compound having C—Cl groups, comprising reacting HF and said saturated or unsaturated compound in the presence of an ionic liquid according to claim 3.

16. Process for the liquid-phase fluorination of a saturated or unsaturated compound having C—Cl groups, comprising reacting HF and said saturated or unsaturated compound in the presence of an ionic liquid according to claim 1.

17. Process for the liquid-phase fluorination of a saturated or unsaturated compound having C—Cl groups, comprising reacting HF and said saturated or unsaturated compound in the presence of an ionic liquid according to claim 5.

18. Process for the liquid-phase fluorination of a saturated or unsaturated compound having C—Cl groups, comprising reacting HF and said saturated or unsaturated compound in the presence of an ionic liquid according to claim 6.

19. Process for the liquid-phase fluorination of a saturated or unsaturated compound having C—Cl groups, comprising reacting HF and said saturated or unsaturated compound in the presence of an ionic liquid according to claim 7.

20. Ionic liquid according to claim 2, wherein the ratio is between 1/1 and 2.5/1.

21. Ionic liquid according to claim 2, wherein the ratio is between 1/1 and 2/1.

22. Ionic liquid according to claim 7, wherein the cation X+ is a trimethylsulphonium cation.

23. Ionic liquid according to claim 13, wherein the cation X+ is a trimethylsulphonium cation.

24. Ionic liquid according to claim 3, in which the Lewis acid is an antimony-comprising compound.

25. Ionic liquid according to claim 3, wherein the Lewis acid is $TiCl_4$, $TaF_5$, $SbFCl_4$, $SbF_2Cl_3$, $SbF_3Cl_2$, $SbF_4Cl$ or $SbF_5$.

26. Ionic liquid according to claim 1, wherein the cation $X^+$ is N-ethylpyridinium, N-butylpyridinium, 1-ethyl-3-methylimidazolium or 1-butyl-3-methylimidazolium cation.

* * * * *